United States Patent
Rowston

(10) Patent No.: US 9,700,666 B2
(45) Date of Patent: Jul. 11, 2017

(54) MEDICAL PARAPHERNALIA CARRIER ASSEMBLY

(71) Applicant: Phillip Rowston, Cabarita Beach (AU)

(72) Inventor: Phillip Rowston, Cabarita Beach (AU)

( * ) Notice: Subject to any disclaimer, the term of this patent is extended or adjusted under 35 U.S.C. 154(b) by 0 days.

(21) Appl. No.: 14/416,757

(22) PCT Filed: Jul. 25, 2013

(86) PCT No.: PCT/AU2013/000818
§ 371 (c)(1),
(2) Date: Jan. 23, 2015

(87) PCT Pub. No.: WO2014/015373
PCT Pub. Date: Jan. 30, 2014

(65) Prior Publication Data
US 2015/0182690 A1    Jul. 2, 2015

(30) Foreign Application Priority Data
Jul. 25, 2012    (AU) ................ 2012903185

(51) Int. Cl.
*A61M 5/14*    (2006.01)
*F16M 13/02*    (2006.01)
*A61G 7/05*    (2006.01)

(52) U.S. Cl.
CPC ......... *A61M 5/1415* (2013.01); *A61G 7/0503* (2013.01); *A61M 5/1413* (2013.01); *A61M 5/1414* (2013.01); *F16M 13/022* (2013.01)

(58) Field of Classification Search
CPC .............. A61M 5/1415; A61M 5/1414; A61M 5/1417; A61G 7/0503; F16M 13/022
USPC ................. 211/85.13; 248/518, 125.8, 125.9
See application file for complete search history.

(56) References Cited

U.S. PATENT DOCUMENTS

| | | | |
|---|---|---|---|
| 1,231,452 A | 6/1917 | Sword | |
| 1,795,296 A * | 3/1931 | De Zeng | A61B 19/0256 211/85.13 |
| 1,865,757 A | 7/1932 | Honsowetz | |
| 4,489,454 A | 12/1984 | Thompson | |
| 4,593,422 A | 6/1986 | Wolpert, Jr. et al. | |
| 4,673,154 A | 6/1987 | Darapita | |
| 4,700,922 A | 10/1987 | Gross | |
| 4,795,122 A | 1/1989 | Petre | |
| 4,875,651 A | 10/1989 | Wergin et al. | |
| 4,905,944 A * | 3/1990 | Jost | A61M 5/1415 248/125.8 |
| 4,945,592 A | 8/1990 | Sims et al. | |
| 5,366,191 A | 11/1994 | Bekanich | |
| 5,407,163 A | 4/1995 | Kramer et al. | |

(Continued)

OTHER PUBLICATIONS

PCT/AU2013/000818; PCT International Search Report, Sep. 9, 2013.
PCT/AU2013/000818;PCT International Search Report, Sep. 9, 2013.

*Primary Examiner* — Michael Safavi
(74) *Attorney, Agent, or Firm* — Eagar & Martin Pty Ltd

(57) ABSTRACT

A medical paraphernalia carrier assembly for carrying medical paraphernalia adjacent a patient care bed includes a base assembly and a paraphernalia support assembly. A coupling assembly couples the base assembly and the paraphernalia support assembly in a manner that permits the paraphernalia support assembly to be displaceable between lateral sides of a bed when the base assembly is located intermediate the lateral sides of the bed.

10 Claims, 13 Drawing Sheets

(56) References Cited

U.S. PATENT DOCUMENTS

| | | | | |
|---|---|---|---|---|
| 5,470,037 A * | 11/1995 | Willis | A61G 7/0503 | 248/125.9 |
| 5,499,721 A * | 3/1996 | Hansen | A61G 7/0503 | 211/113 |
| 6,056,249 A * | 5/2000 | Fillon, Jr. | A61M 5/1415 | 248/125.7 |
| 6,471,167 B1 * | 10/2002 | Myers | A61B 19/0271 | 248/125.9 |
| 6,796,536 B1 * | 9/2004 | Sevier, IV | A47B 23/046 | 248/121 |
| 6,966,086 B2 | 11/2005 | Metz et al. | | |
| 6,971,617 B2 | 12/2005 | Nguyen | | |
| 7,040,591 B1 * | 5/2006 | Simon | A47B 23/04 | 248/122.1 |
| 7,195,215 B2 * | 3/2007 | Lin | F16M 11/04 | 248/125.9 |
| 7,207,531 B2 * | 4/2007 | Piontkowski | A61B 19/26 | 248/122.1 |
| 7,314,200 B2 | 1/2008 | Bally et al. | | |
| 7,533,428 B2 | 5/2009 | Yunker | | |
| 7,594,633 B2 * | 9/2009 | Carnevali | F16M 11/04 | 248/125.9 |
| 7,669,813 B2 * | 3/2010 | Crain | G01C 15/06 | 248/163.1 |
| 7,735,788 B2 | 6/2010 | Newkirk et al. | | |
| 7,748,672 B2 | 7/2010 | Walke | | |
| 7,798,456 B2 | 9/2010 | Newkirk et al. | | |
| 7,845,601 B1 * | 12/2010 | Culpepper | A61G 7/05 | 248/125.2 |
| 8,104,729 B2 | 1/2012 | Walke et al. | | |
| 8,272,604 B2 * | 9/2012 | Foster | B60R 11/0252 | 248/124.1 |
| 8,443,472 B2 * | 5/2013 | Sherman | A47C 21/00 | 248/125.8 |
| 2002/0162926 A1 * | 11/2002 | Nguyen | A61G 13/101 | 248/229.25 |
| 2006/0255215 A1 * | 11/2006 | Carnevali | F16B 7/14 | 248/125.8 |
| 2007/0023587 A1 * | 2/2007 | Eggleston | A61G 12/008 | 248/98 |
| 2008/0061195 A1 * | 3/2008 | Carnevali | F16M 11/14 | 248/125.8 |
| 2013/0200023 A1 * | 8/2013 | Brotzman | A61B 19/0248 | 211/85.13 |

* cited by examiner

MEDICAL PARAPHERNALIA CARRIER ASSEMBLY

CROSS REFERENCE TO RELATED APPLICATION

This application is a national stage entry of PCT/AU2013/000818 filed on Jul. 25, 2013, which in turn claims the benefit of priority from Australian Patent Application No. 2012903185 filed on Jul. 25, 2012. Each of the foregoing patent applications is incorporated by reference herein in its entirety for any purpose whatsoever.

FIELD

Various embodiments of a medical paraphernalia carrier assembly and a bed incorporating the medical paraphernalia carrier assembly are described herein.

SUMMARY

Various exemplary embodiments of a medical paraphernalia carrier assembly for carrying medical paraphernalia adjacent a patient care bed comprises:
a base assembly;
a paraphernalia support assembly; and
a coupling assembly for coupling the base assembly and the paraphernalia support assembly in a manner that permits the paraphernalia support assembly to be displaceable between lateral sides of a bed when the base assembly is located intermediate the lateral skies of the bed.

The base assembly may include a mounting arrangement to mount the base assembly on a head end of a bed frame. The mounting arrangement may include a clamp assembly or arrangement for clamping onto the head-end part.

In another embodiment, the mounting arrangement may include a base for mounting onto a substrate, such as a floor, adjacent the head end and intermediate lateral sides of the bed.

The base assembly may include a post that extends from the mounting arrangement. The post may be longitudinally upright, in use.

The coupling assembly may include a first swivel coupling arranged on the post. An extension arm may interconnect the first swivel coupling and the paraphernalia support assembly. The extension arm may be generally orthogonal to the post. It follows that the base assembly and the paraphernalia support assembly may be offset from each other by the extension arm, with the extension arm being able to swivel relative to the post. The extension arm may be dimensioned so that the paraphernalia support assembly can be swiveled to provide functional access from either side of the bed.

The first swivel coupling may include a lower annular flange that is mounted on the post intermediate ends of the post. The swivel coupling may include a tubular carrier. An upper annular flange may be mounted on an end of the carrier. The post may be partially received in the carrier to bring the flanges into alignment and sliding engagement with each other.

The first swivel coupling may include a positive mechanical locking mechanism, for locking the post and the extension arm in a position relative to each other, able to be released from each other to swivel. The locking mechanism may include a pin that projects through one flange and into any one of a plurality of holes along a pitch circle in the other flange. The locking mechanism may include a biasing mechanism that urges the pin into engagement with the other flange, the pin being manually displaceable against a bias of the biasing mechanism to release the flanges to permit swiveling of the flanges relative to each other.

The paraphernalia support assembly may include a holder to retain or hold an item of medical paraphernalia. The holder may be cylindrical and tubular. For example, a stem of an IV support may be received in the holder. The holder may cooperate with the coupling assembly to be in a longitudinally upright position, in use. In other embodiments, the holder can be configured to support other items of medical paraphernalia.

The paraphernalia support assembly may include a support member that is pivotally or rotationally mounted on the holder. The support member may be configured for supporting one or more items of medical equipment, such as monitors and pumps. Thus, an orientation of such equipment can be adjusted when the position of the paraphernalia support assembly is adjusted.

The support member may be an elongate support tube. A second swivel coupling may be arranged between the support tube and the holder. The second swivel coupling may include a lower annular flange mounted on the holder, intermediate ends of the holder. An upper annular flange may be mounted on a lower end of the support tube. The holder may be received through the support tube to bring the flanges into alignment and sliding engagement with each other.

The second swivel coupling may also include a positive mechanical locking mechanism, for locking the support tube and the holder in a position relative to each other, able to be released from each other to swivel. The locking mechanism may include a pin that projects through one flange and into any one of a plurality of holes along a pitch circle in the other flange. The locking mechanism may include a biasing mechanism that urges the pin into engagement with the other flange, the pin being manually displaceable against a bias of the biasing mechanism to release the flanges to permit swiveling of the flanges relative to each other.

Various exemplary embodiments provide a patient care bed that is equipped with a medical paraphernalia carrier assembly as defined above.

The medical paraphernalia carrier assembly may include any one or more optional features as herein defined, described, and illustrated.

DESCRIPTION OF EMBODIMENTS

Figure 1:
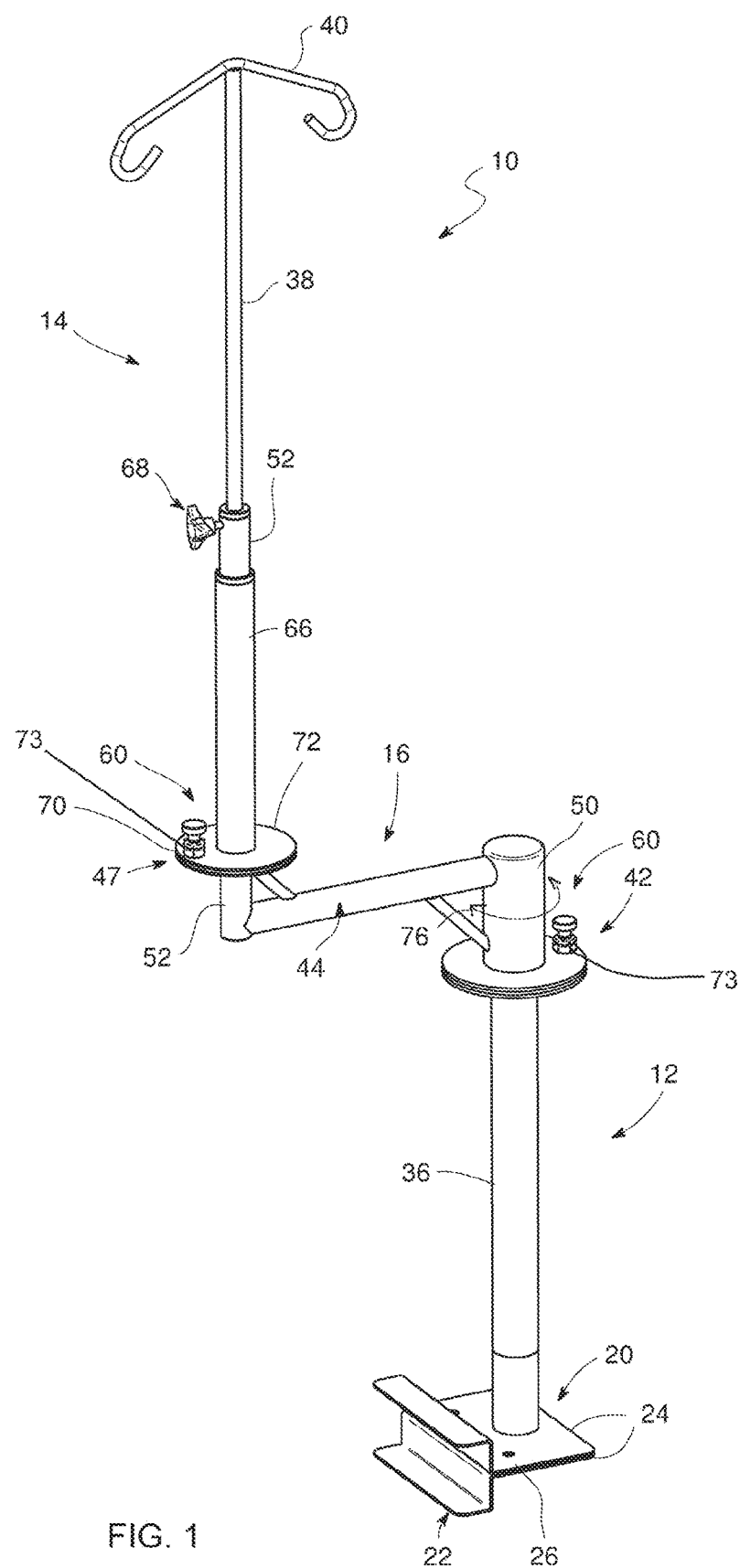
FIG. 1 shows a three-dimensional view of an exemplary embodiment of a medical paraphernalia carrier assembly.
Figure 4:
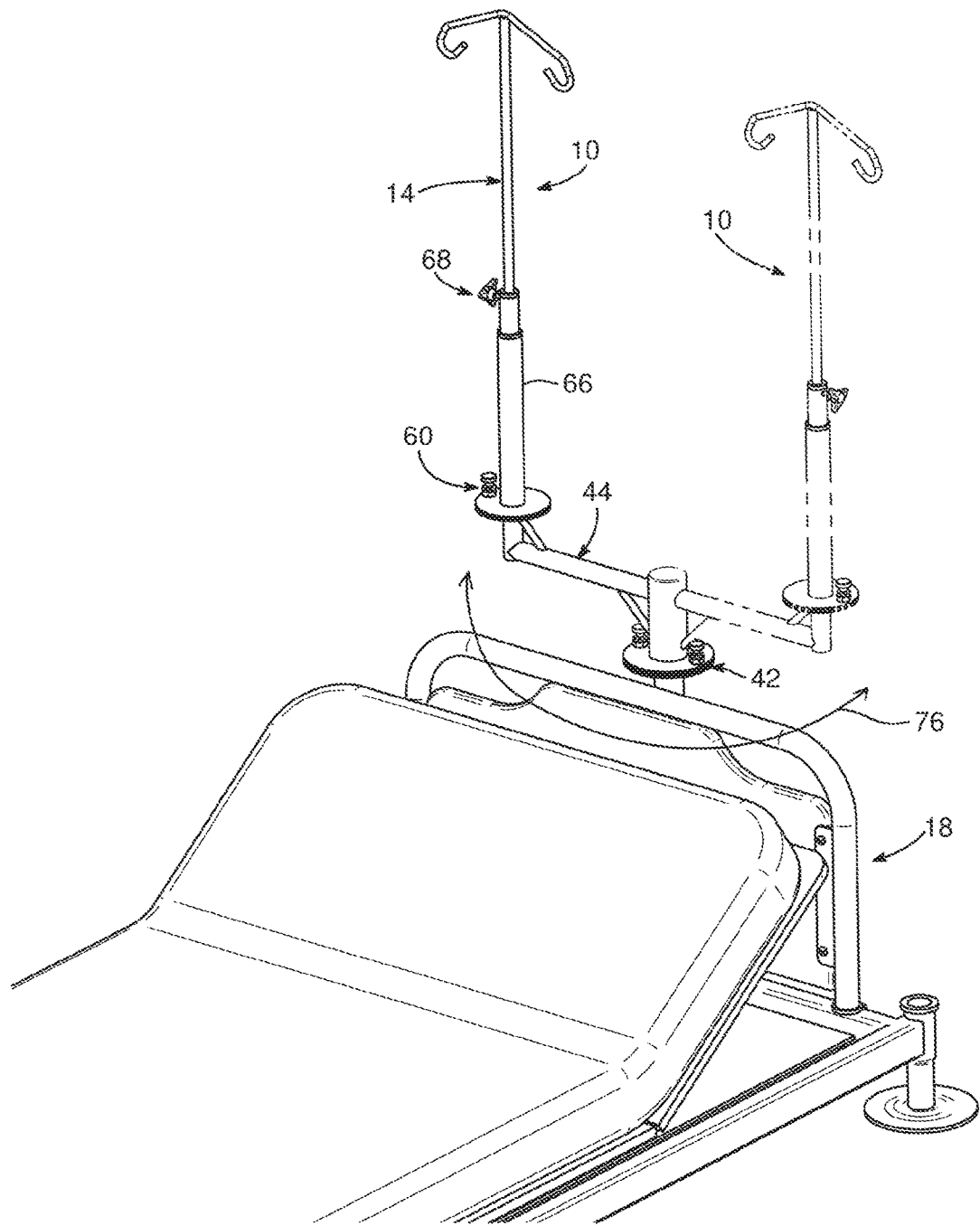
FIG. 4 shows a patient care bed that is equipped with the medical paraphernalia carrier assembly in FIG. 2.
Figure 5:
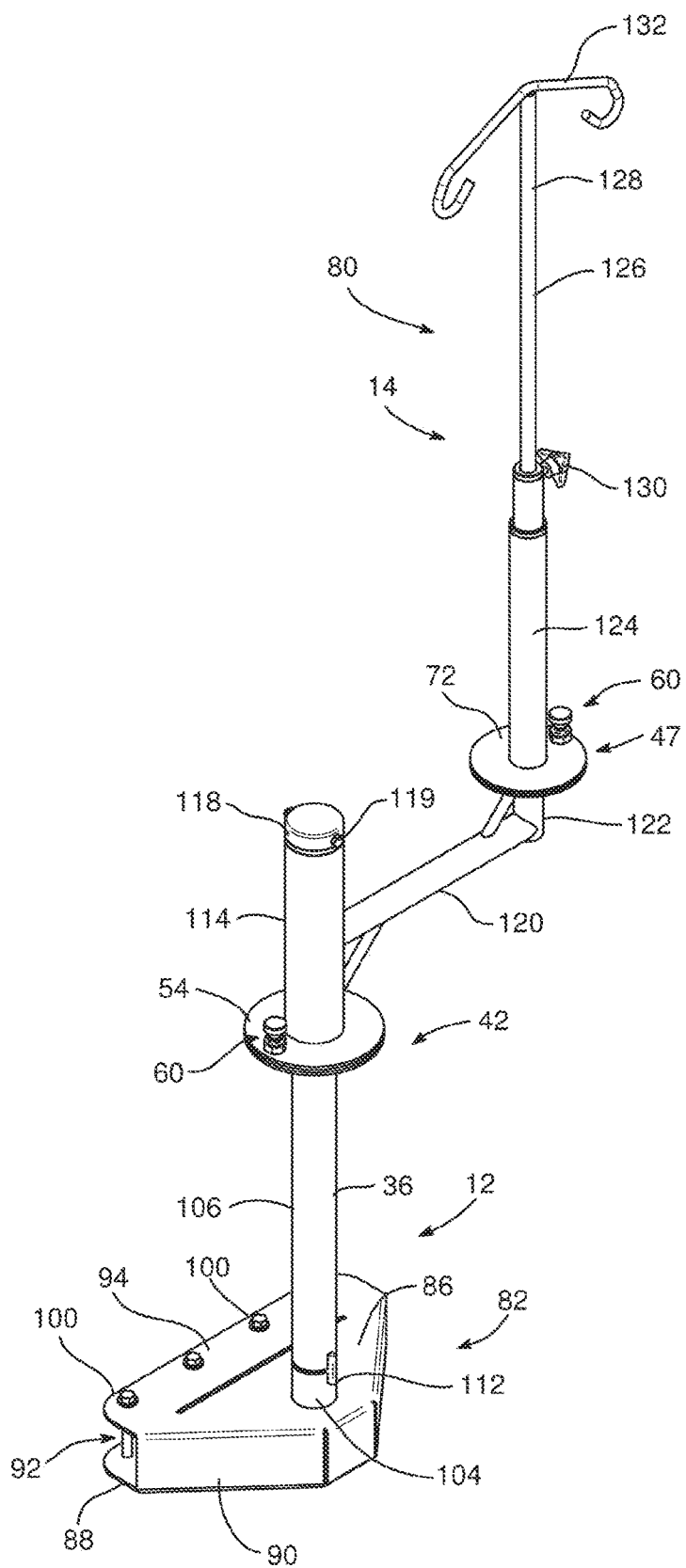
FIG. 5 shows a rear, three-dimensional view of an exemplary embodiment of a medical paraphernalia carrier assembly.
Figure 6:
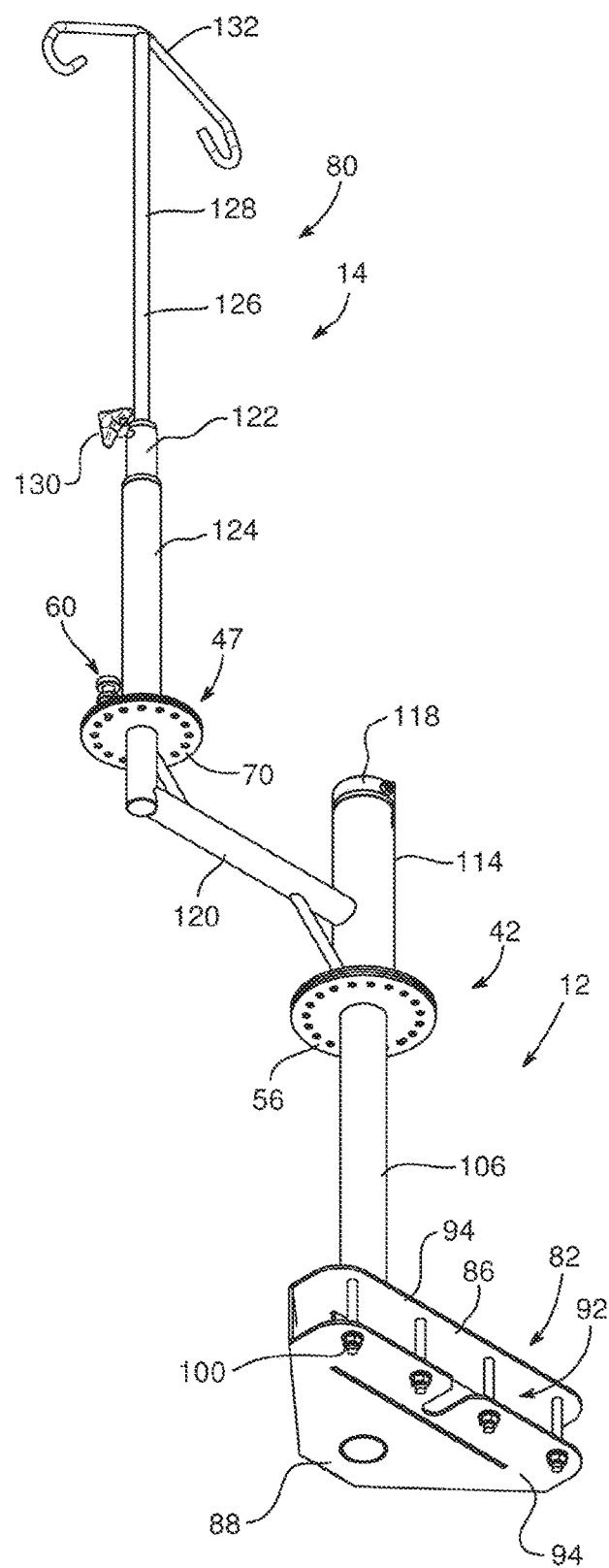
FIG. 6 shows a front, three-dimensional view of the carrier assembly of FIG. 5.
Figure 7:
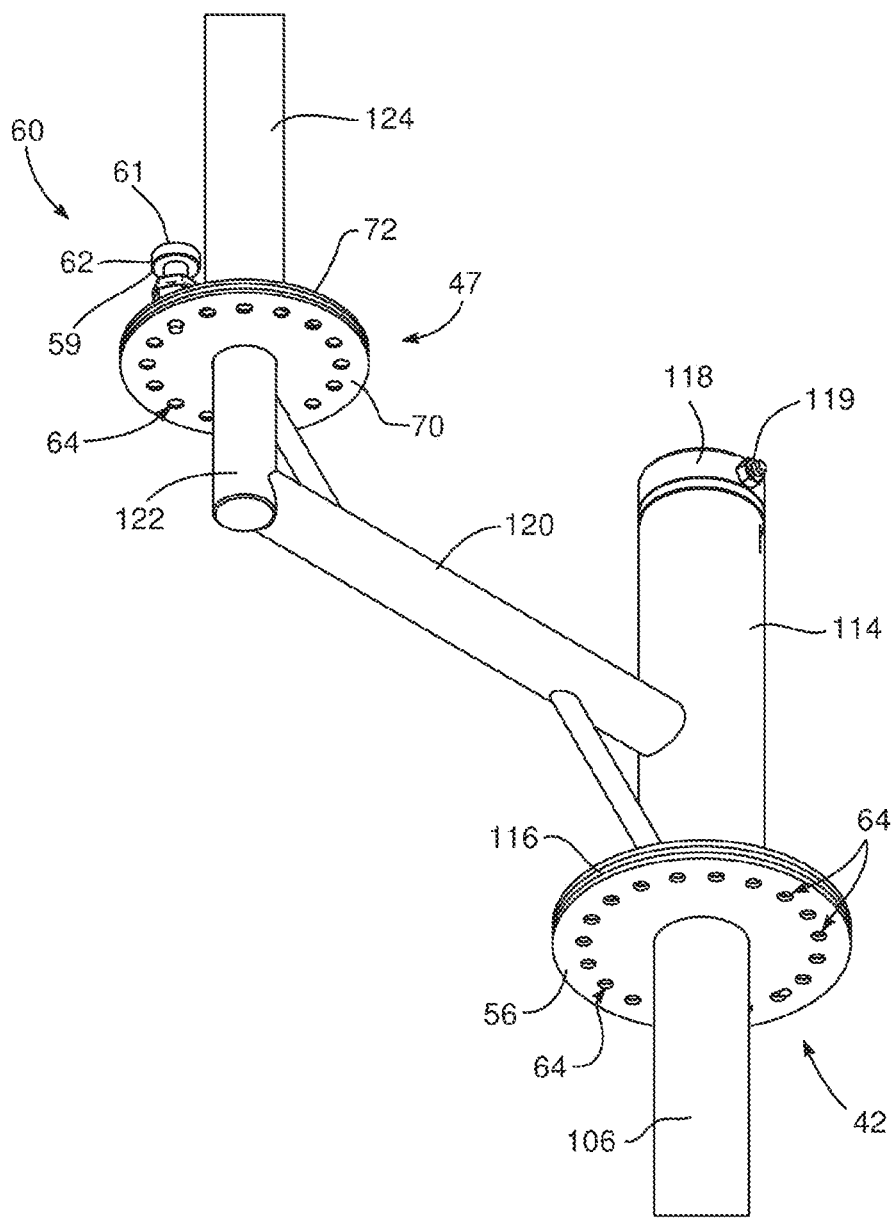
FIG. 7 shows a view from below of a coupling assembly of the carrier assembly.
Figure 8:
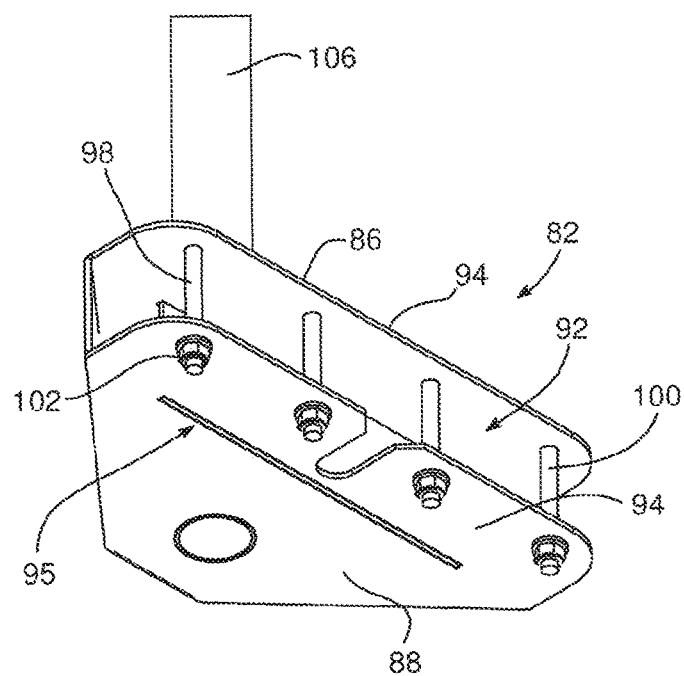
FIG. 8 shows a front view of a clamp assembly of the carrier assembly for clamping the carrier assembly to a bed frame.
Figure 9:
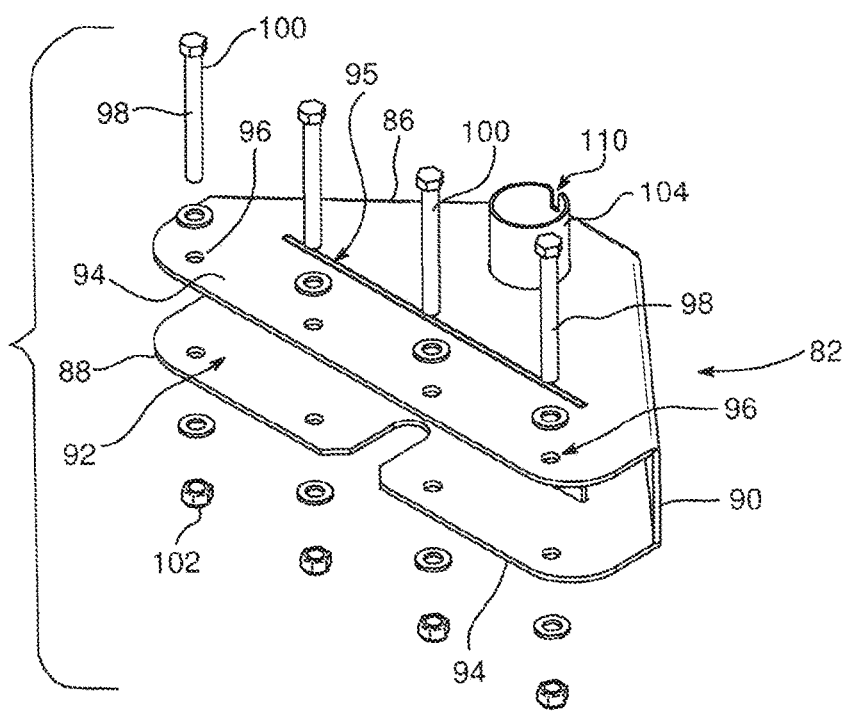
FIG. 9 shows a disassembled or exploded view of the clamp assembly.

Referring to FIG. 1, reference numeral 10 generally indicates an exemplary embodiment of a medical paraphernalia carrier assembly for carrying medical paraphernalia (not shown) adjacent a patient care bed 18. Broadly, the carrier assembly 10 includes a base assembly 12, a paraphernalia support assembly 14, and a coupling assembly 16 for coupling the base assembly 12 and the paraphernalia support assembly 14 in a manner that permits the paraphernalia support assembly 14 to be displaceable between lateral sides of the bed 18 when the base assembly 12 is located intermediate lateral sides of the bed 18 (FIG. 4).

In this embodiment, the paraphernalia carrier assembly 10 is configured for supporting or suspending an intravenous medicine bag and optionally, one or more medical devices, such as a monitors, pumps and similar equipment.

The base assembly 12 includes a mounting arrangement 20 for mounting the base assembly 12 on a head end of a bed frame of the bed 18 intermediate lateral sides of the bed. The mounting arrangement 20 is in the form of a clamp 20 for clamping onto the head-end part of the bed frame of the bed 18. The clamp 20 includes two stepped clamp plates 24 that define a mouth 22. The clamp plates 24 define bolt holes 26 for bolting the clamp plates 24 together for clamping onto the bed frame of the bed 18.

The base assembly 12 includes a post 36 that extends from the clamp 20, so that the post 36 is longitudinally upright, in use. The post 36 is formed from a tube such as a medical grade stainless steel pipe.

Figure 2:
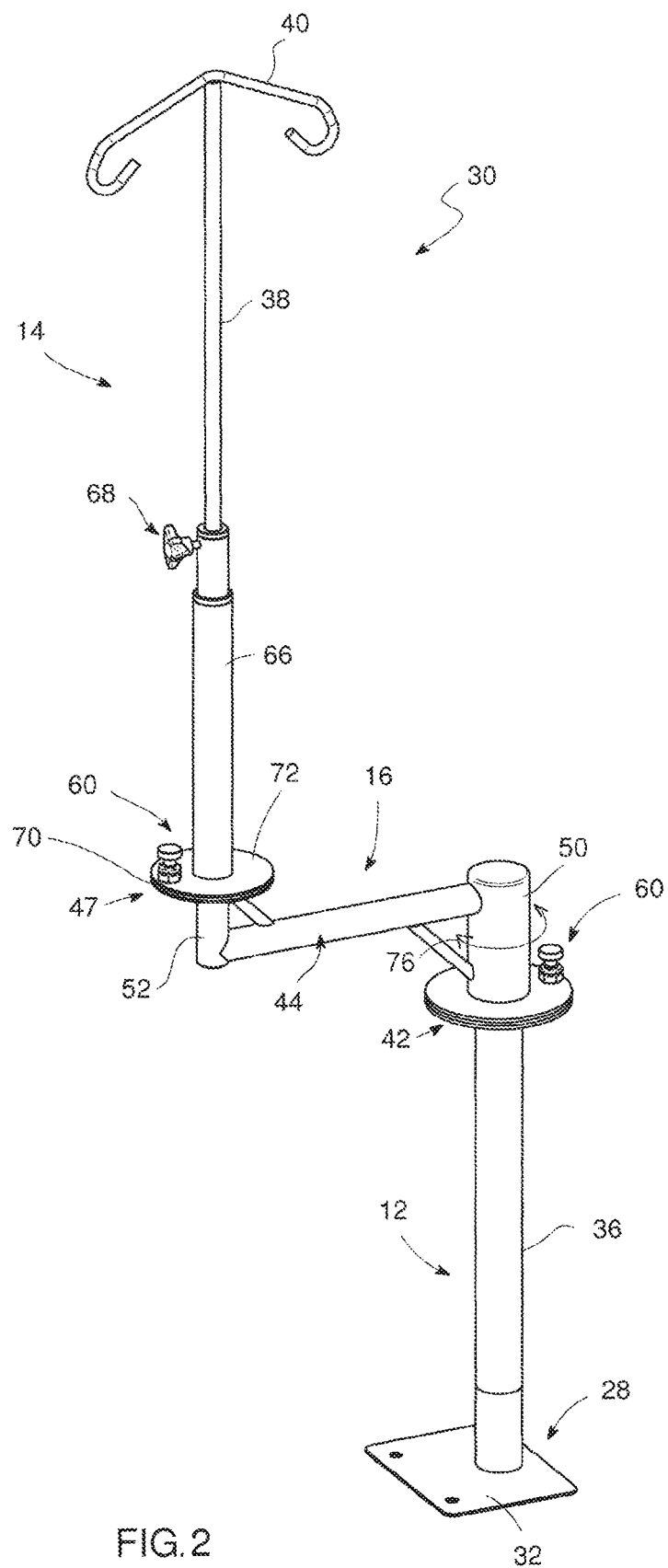
FIG. 2 shows a three-dimensional view of another exemplary embodiment of a medical paraphernalia carrier assembly.

FIG. 2 shows another embodiment of a medical paraphernalia carrier assembly 30. With reference to FIG. 1, like reference numerals refer to like parts, unless otherwise specified.

The assembly 30 includes a base assembly 12 having a mounting arrangement 28. The arrangement 28 includes a base plate 32 for bolting into a substrate or floor adjacent a head of the bed 18.

The paraphernalia support assembly 14 includes a holder 52 for holding an item of medical paraphernalia. The holder 52 is cylindrical and tubular. A stem 38 of an IV support 40 is held in the holder 52. The holder 52 cooperates with the coupling assembly 16 so that the holder 52 and thus the stem 38 are oriented in a longitudinally upright position, in use, as is explained in more detail below.

The coupling assembly 16 includes a swivel coupling 42 arranged on the post 36. An extension arm 44 extends from the swivel coupling 42 generally orthogonally relative to the post 36. The holder 52 is connected to the arm 44 to extend generally orthogonally with respect to the arm 44.

It follows that the base assembly 12 and the paraphernalia support assembly 14 are longitudinally offset from each other by the extension arm 44 and the extension arm 44 is able to swivel relative to the base member 12.

The extension arm 44 is of sufficient length to permit functional access from either side of the bed 18 when the support assembly 14 is swung or pivoted to that side of the bed 18.

The extension arm 44 interconnects a cylindrical carrier 50 and a portion 58 of the tube 66 that project transversely in opposing directions away from respective ends of the arm 44.

Figure 3:
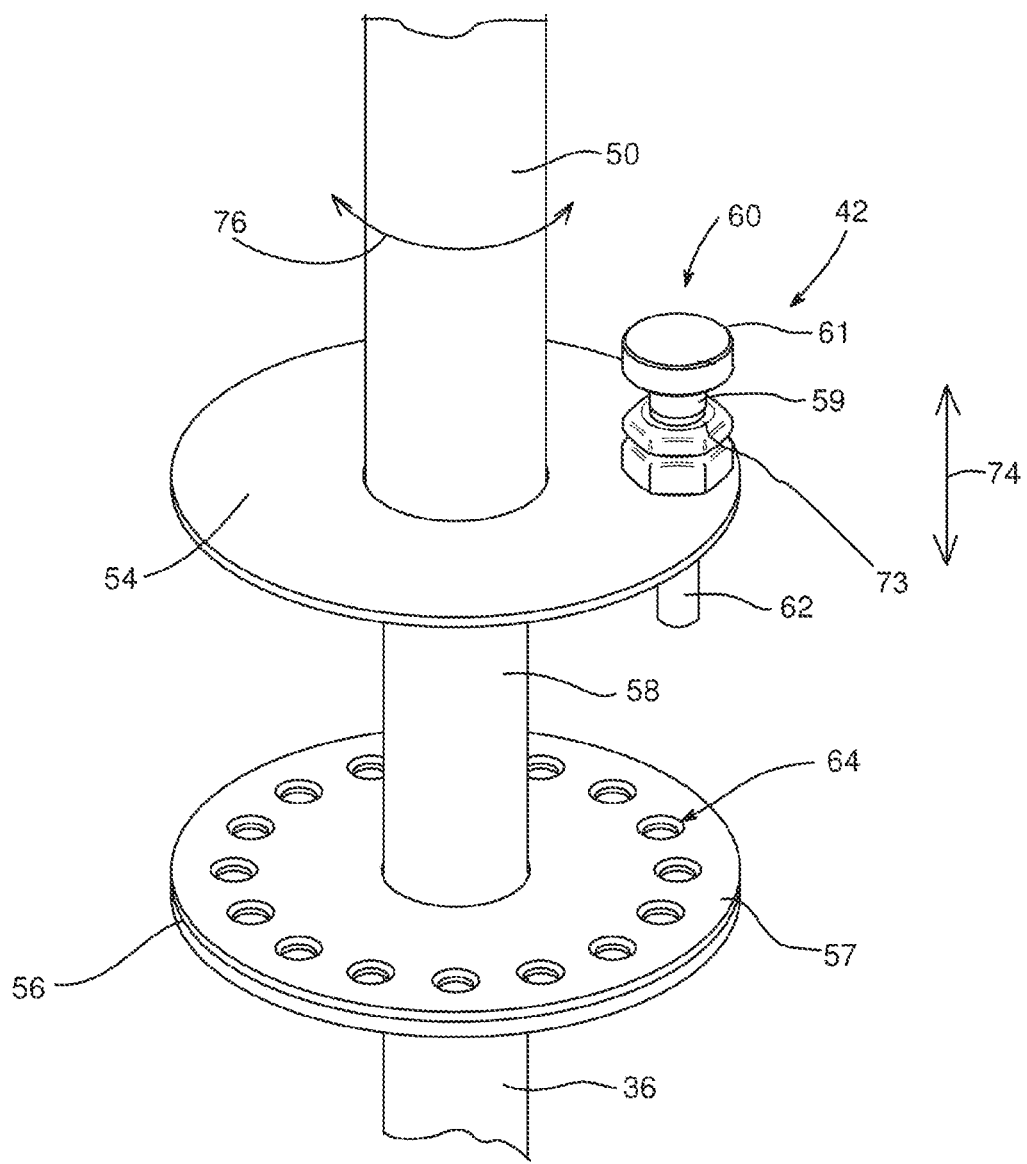
FIG. 3 shows three-dimensional partly exploded view of a swivel coupling that forms part of the medical paraphernalia carrier assemblies in FIGS. 1 and 2.

The swivel coupling 42 includes two conterminous annular flanges 54, 56 (FIG. 3) in the form of an upper flange 54 and a lower flange 56. The upper flange 54 is connected to the carrier 50. The lower flange 56 is connected to an upper end of the post 36. A portion 58 of the carrier 50 is received in the post 36 so that the flanges 54, 56 can engage each other. It will be appreciated that the portion 58 can also be in form of a suitable, discrete insert. In that case, the flanges 54, 56 would be on respective ends of post 36 and the carrier 50.

Thus, the carrier 50 and the post 36 can swivel relative to each other with the flanges 54, 56 in sliding engagement.

The swivel coupling 42 includes a positive mechanical locking mechanism 60 for locking the base assembly 12 and the extension arm 44 in a selected position relative to each other, able to be released from each other to swivel.

The locking mechanism 60 includes a pin 62 that projects through the upper flange 54 and through any one of a plurality of holes 64 along a pitch circle in the lower flange 56. It will be appreciated this could be reversed with the pin projecting through the lower flange 56 and through any one of a plurality of holes in the upper flange 54.

The locking mechanism 60 includes a biasing mechanism 73, for example a spring that urges the pin 62 into engagement with the lower flange 56. The pin 62 is manually displaceable against a bias of the spring to release the flanges 54, 56 to permit swiveling of the flanges 54, 56 relative to each other.

A grip 61 is arranged on an end of the pin 62 so that a user can manipulate the pin 62.

The locking mechanism 60 can be a lock pin mechanism of the type in which the pin 62 is lifted and rotated to be retained in the lifted condition against the bias of a spring. Counter-rotation of the pin 62 disengages the pin 62 and allows the pin to be driven by the spring into engagement with a hole. It will be appreciated that such a lock pin mechanism is conventional and so further description is not required.

The stem 38 and the holder 52 are telescopically displaceable relative to each other. A locking mechanism 68, in the form of a grub-screw can be used to lock the stem 38 relative to the holder 52. Thus, a height of the IV support 40 is adjustable.

The paraphernalia support assembly 14 includes a support member in the form of a support tube 66. The tube 66 is configured to permit medical equipment, such as monitors and pumps and the like to be connected to the tube 66 in a conventional manner.

A flange 70 is mounted on the holder 52, intermediate ends of the holder 52. A flange 72 is mounted on a lower end of the tube 66 so that the flanges 70, 72 can engage each other when the holder 52 is received through the tube 66. Thus, the holder 52 and the tube 66 can be coupled with a swivel coupling 47 in a manner similar to that described above with reference to the swivel coupling 42. It follows that the medical equipment connected to the tube 66 can be pivoted into a desired position to accommodate pivotal movement of the arm 44.

The swivel coupling 47 also includes a positive locking mechanism in the form of the lock pin mechanism 60. It follows that the operation of the swivel coupling 47 is the same as that of the swivel coupling 42. Reference numerals used in connection with the coupling 47 refer to the same components as those used in connection with the coupling 42, for convenience.

A bearing disk or washer 57 is interposed between the flanges 54 and 56. The washer 57 is formed from a material that facilitates sliding of the flanges relative to the bearing disk or washer 57. The bearing disk or washer 57 can be formed from a synthetic plastic material, such as Nylon. Such a disk or washer can also be interposed between the flanges 70, 72.

In use, the carrier assembly 10 is mounted with the clamp 20 onto a bed frame of a bed 18 at a head end and intermediate lateral sides of the bed 18. As shown in FIG. 4, the swivel coupling 42 is positioned between lateral sides of the bed 18, so that it can be reached by a user from either side of the bed 18 near the head end of the bed 18.

The pin 62 is gripped and pulled upwardly (see arrow 74 in FIG. 3), which releases the flanges 54, 56 from each other. The pin 62 can be turned to retain it in the lifted condition.

A user then swings (see arrow 76) the extension arm 44, and thus the support assembly 14 towards either lateral side of the bed, as needed. When the pin 62 is released, it engages the relevant hole in the bottom flange 56 to lock the flanges 54, 56 to each other.

When medical equipment is mounted on the tube 66, the pin 62 associated with the flanges 70, 72 can also be manipulated to allows the flanges 70, 72 to rotate relative to each other. This allows the medical equipment to be positioned correctly to accommodate the change in position of the extension arm 44.

In some embodiments, the pin 62 will automatically engage a hole if it is released while the extension arm 44 is pivoted. This serves as a safety feature in the event that a user lifts the pin 62 and releases it prematurely. Instead of swinging around freely, the pin 62 is biased into engagement with a hole to lock the arm 44 positively against such swinging. It will be appreciated that in a medical care facility a freely swinging IV stand could be extremely dangerous. Thus, the locking mechanism 60 serves to alleviate or mitigate that danger. It will be appreciated that an arrangement in which a user is required manually to release, position and re-tighten a locking mechanism cannot provide such a safety mechanism. In such arrangements, it is possible that a carer or the like may forget to tighten the locking mechanism. Should such an arrangement be bumped or simply move, for example when the bed is shifted, the resultant swinging can be dangerous and can cause harm. The safety mechanism provided by the mechanism 60 is particularly suited to areas in which a high level of activity may occur.

A shank 59 of the pin 62 can be brightly coloured, for example coated with a high-visibility paint or material. Thus, it will be readily apparent to personnel in the vicinity of the patient bed 18 that the pin 62 is disengaged since the pin 62 will be in a lifted condition exposing the shank. In one embodiment, the pin 62 can be dimensioned so that when the pin 62 engages the flange 56, the grip 61 is flush with the flange 54. Thus, the high visibility material is immediately discernible when the pin 62 is lifted. The carrier assembly 10, 30 can then be adjusted to allow the pin 62 to engage a hole. In some embodiments, that can be done without having to grasp the pin 62.

Simply lifting the pin 62 and allowing it to drop into an appropriate hole is simpler and easier than loosening and subsequently tightening a locking arrangement. The simplicity is enhanced by the positive locking mechanism. In busy medical areas, it is undesirable for medical personnel to have to concentrate on a position of a medical carrier assembly. The mechanisms described above allow adjustment and positive locking in a manner that is simple and convenient compared to twisting mechanisms that are often used to lock or secure cylindrical components together, for example.

In other embodiments (not shown) the extension arm and/or the base may also be configured so that they are lengthwise adjustable.

The carrier assembly 10 is useful for repositioning the IV support formation 40 and medical equipment at either side of the bed as needed. The locking mechanism 60 is easily operated to enable repositioning of the IV support formation 40 and is useful for locking the IV support formation 40 in position.

The base assembly 12 is formed for mounting adjacent the bed 18 in a manner that minimises space usage so as to avoid obstruction with other medical equipment.

The extension arm 44 can swing over the bed 18 between its operative positions. Thus, obstruction with other medical equipment that may be placed around the head-end of the bed 18 is avoided. However, the extension arm 44 can swing either clockwise or counter-clockwise, to accommodate a position of the bed or other circumstances in the vicinity of the bed.

In FIGS. 5 to 14, reference numeral 80 generally indicates an exemplary embodiment of a carrier assembly for medical paraphernalia. With reference to the preceding drawings, like reference numerals refer to like parts, unless otherwise specified.

In the carrier assembly 80, the base member 12 includes a clamp assembly 82 (shown in detail in FIGS. 8 and 9) that is configured to clamp on to a head end frame member 84 of a patient bed frame 85. The clamp assembly 82 includes an upper clamp member 86 and a lower clamp member 88. A sidewall 90 separates the clamp members 86, 88. A clamping zone 92 is defined between the members 86, 88. The frame member 84 can be received in the zone 92 with corresponding portions 94 overhanging the member 84. The corresponding portions 94 define a series of corresponding pairs of openings 96. The corresponding portions 94 are demarcated by slots 95 so that the portions 94 can have a degree of flex to facilitate clamping.

A shank 98 of a bolt 100 is received through each pair of openings 96. A nut 102 is threaded onto each shank 98 so that when the nuts 102 and bolts 100 are tightened, the clamp members 86, 88 are urged together to clamp the frame member 84 in the zone 92. In that condition, the shanks 98 are positioned in front of the frame member 84, further to secure the frame member 84 in the zone 92.

A tubular, cylindrical mounting stub 104 extends from the upper clamp member 86. The post 36 includes a cylindrical tube 106 that is the same or roughly the same diameter as the stub 104. A mounting shaft 108 extends from the tube 106 to be received in the stub 104. The stub 104 defines a peripheral slot 110. A key 112 (FIG. 10) is arranged on the shaft 108 to engage the slot 110 when the shaft 108 is inserted into the stub 104. Thus, rotation of the post 36 relative to the clamp member 86 is inhibited.

The flange 56 is mounted on the tube 106 intermediate ends of the tube 106.

Figure 10:
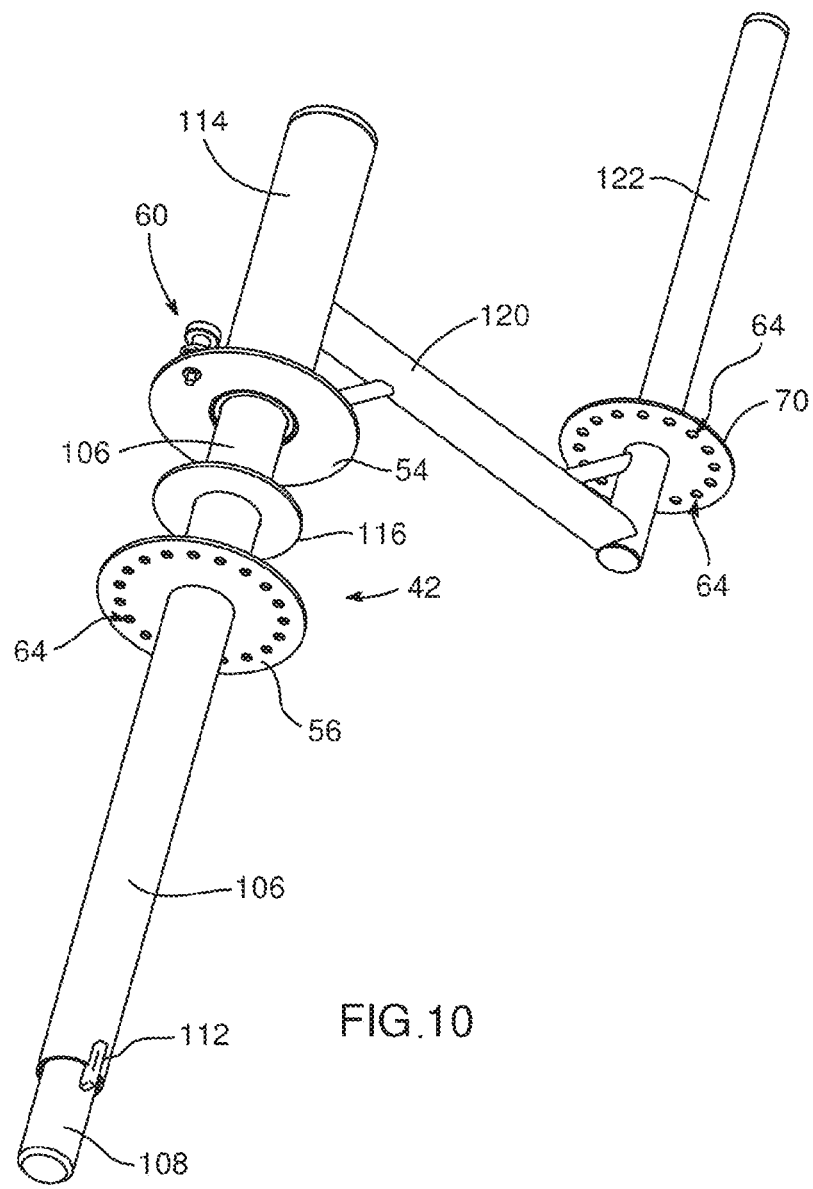
FIG. 10 shows a partly exploded view from underneath of part of the carrier assembly.
Figure 11:
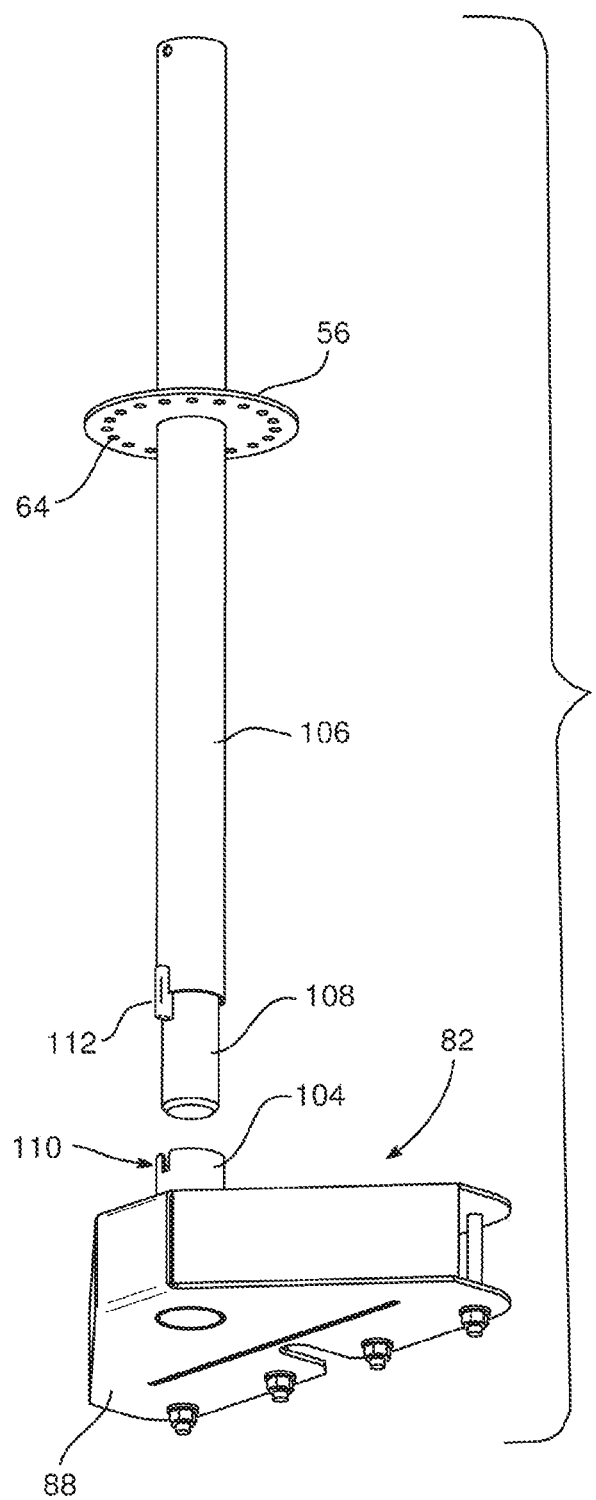
FIG. 11 shows a base assembly of the clamp assembly.
Figures 12, 13:
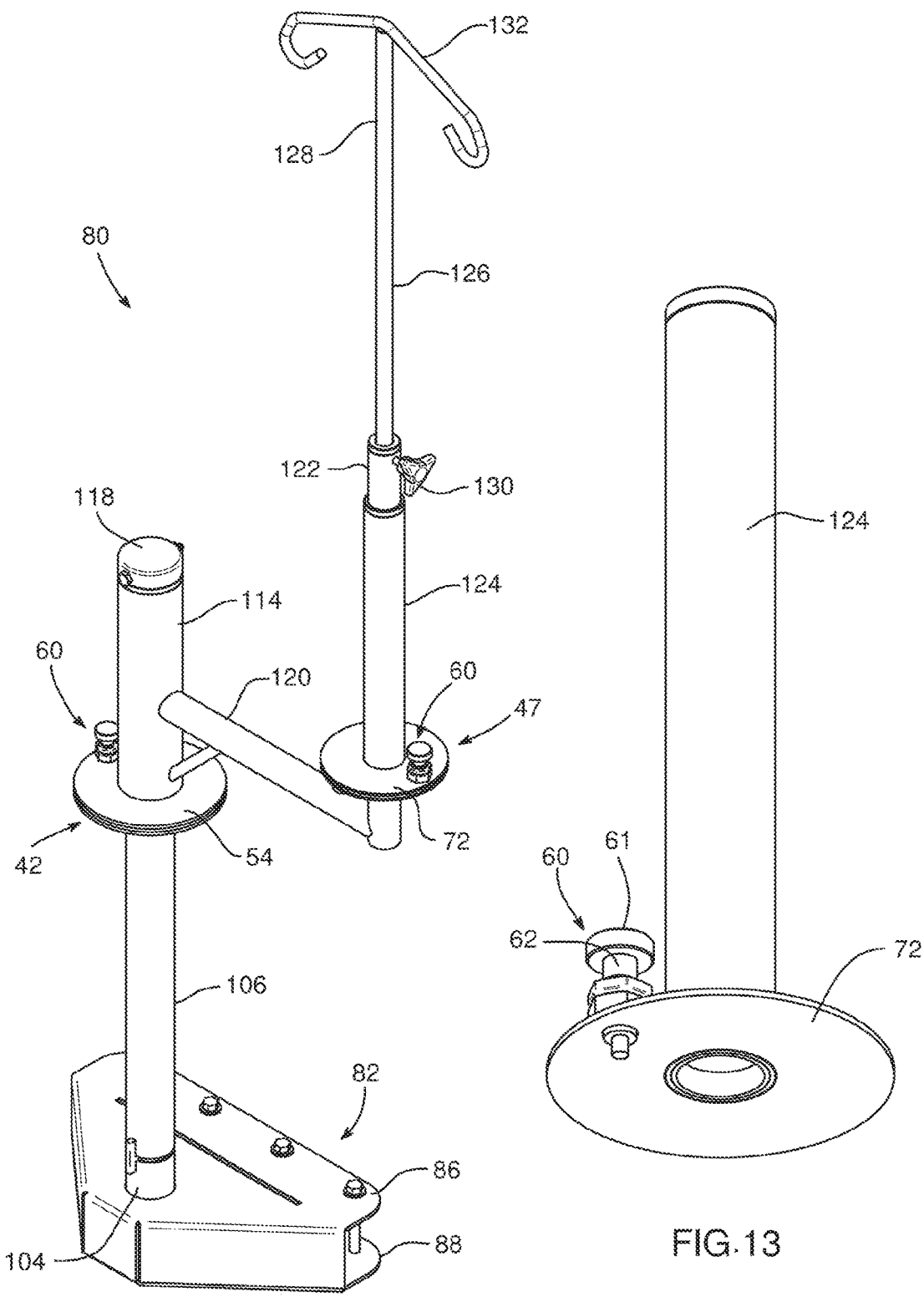
FIG. 12 shows a three-dimensional view, from above, of the carrier assembly.
FIG. 13 shows part of a second swivel coupling of the carrier assembly.

The flange 54 is mounted on an end of a tubular carrier 114. The tube 106 is received in the carrier 114 so that the flanges 54, 56 can engage. The carrier 114 is capable of rotating about the tube 106. A disk-like wear member or washer 116 is arranged on the tube 106 (FIG. 10). The washer 116 is interposed between the flanges 54, 56 when the tube is received in the carrier 114.

A collar 118 is fastened to an upper end of the tube 106 with a nut and bolt arrangement 119. The collar 118 serves to inhibit lifting of the carrier 114 from the tube 106 while permitting rotational movement of the carrier 114. The collar 118 can be of a plastics material, such as nylon or the like.

An arm 120 extends generally orthogonally from the carrier 114. A tubular support holder 122, in turn, extends generally orthogonally from an end of the arm 120. Thus, the holder 122 is generally parallel to the post 36, but offset from the post 36 to an extent determined by a length of the arm 120.

The flange 70 is mounted on the holder 122 intermediate ends of the holder 122.

The carrier assembly 80 includes a tubular support 124 (shown in detail in FIG. 13) to which various items of medical equipment can be connected. Such equipment is presently connected to tubular elements or components of IV stands and the like. Thus, it is unnecessary to describe the manner in which such equipment can be connected to, or supported by the support 124.

The flange 72 is mounted on a bottom end of the support 124.

The holder 122 extends through the support 124 so that the flanges 70, 72 can engage each other in the manner described above.

The holder 122 extends beyond an upper end of the support 124. A stem 126 of an IV support 128 is received in the holder 122. An IV hanger arrangement or formation 132 is arranged on the stem 126.

The stem 126 can slide up or down relative to the holder 122. A grub screw 130 is threaded into the holder 122 to engage the stem 126 so that a height of the formation 132 can be adjusted. A lower end of the holder 122 is closed so that the stem 126 does not inadvertently drop through the holder 122, which could be dangerous.

The various components of the support can be fabricated from any suitable material. For example, where required, the components can be fabricated from stainless steel. Instead, the components can be chrome plated steel.

Figure 14:
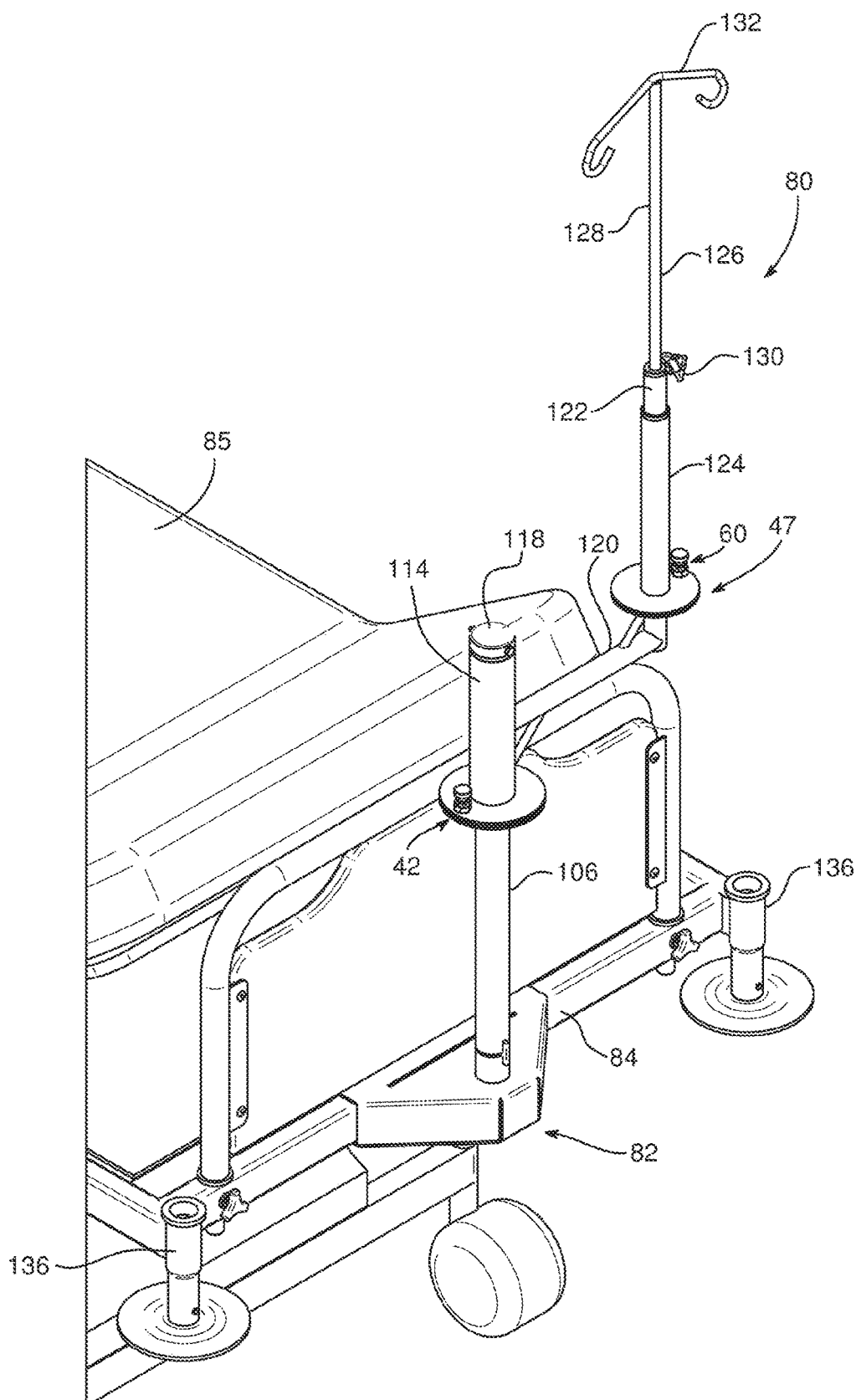
FIG. 14 shows one view of the carrier assembly mounted on a patient bed.
Figure 15:
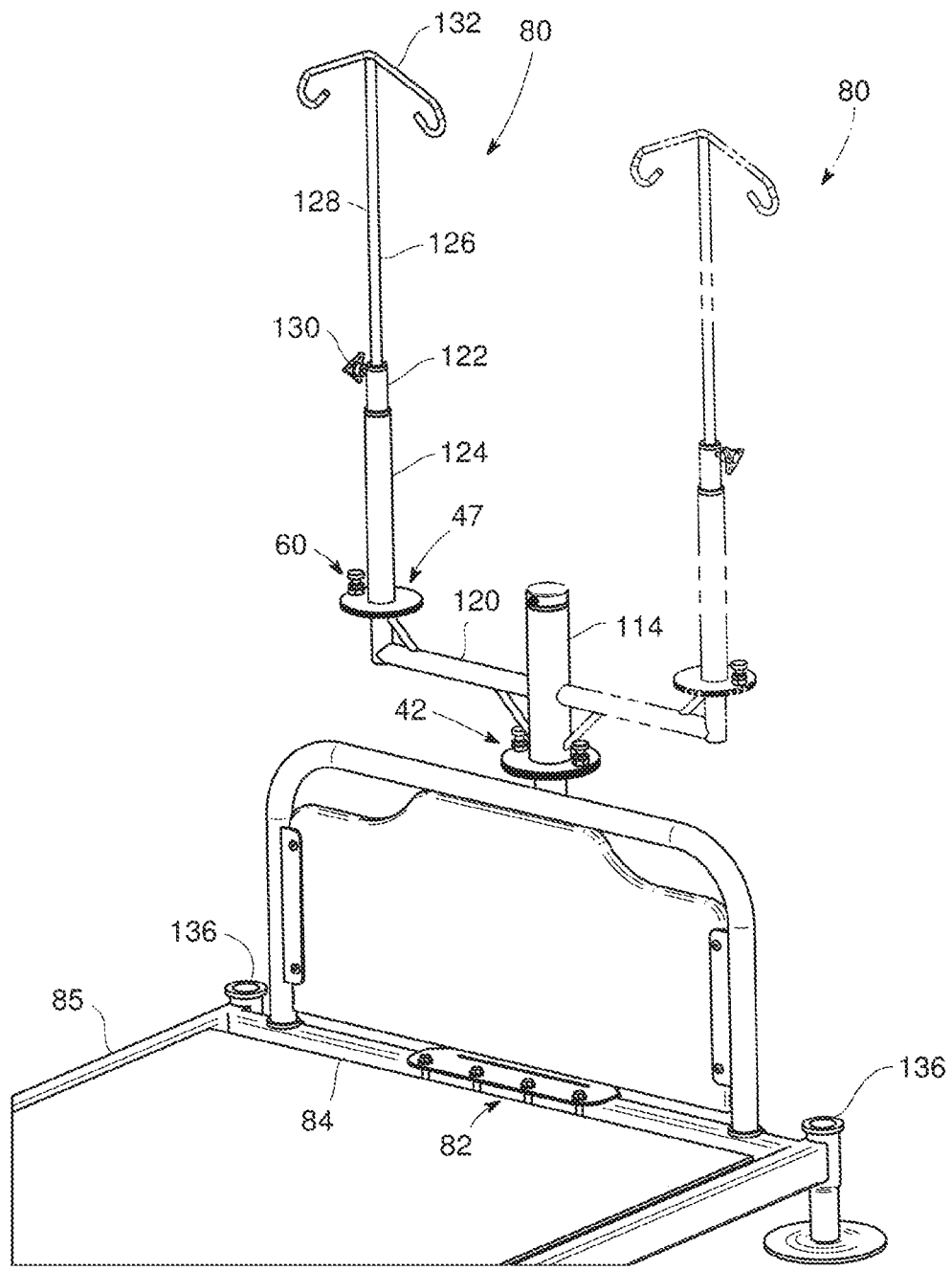
FIG. 15 shows an exemplary embodiment of a medical paraphernalia carrier assembly mounted on a patient bed.

The manner in which the carrier assembly 80 is used is shown in FIGS. 14 and 15. In FIG. 15, the broken lines indicate an alternative position of the assembly 80 that can be achieved, where required. In the event that medical equipment is mounted on the support 124, the flanges 70, 72 can be released from each other by lifting the pin 62 and rotating the support 124 so that the medical equipment is correctly positioned once the arm 120 has been swung into the new position.

It can be the case that the bed 18 can include two sockets 136, one on each side of the bed 18. These can be mounted to corners of the bed frame 85 at the head end of the bed 18. Each socket 136 is dimensioned to accommodate a base of a conventional IV stand. Conventionally, when it becomes necessary to adjust a position of the IV stand, the IV stand needs to be lifted out of one of the sockets 136 and placed into the other socket. This can be cumbersome and can also lead to back or other physical injury. As can be seen in FIG. 15, the assembly 80 can be adjusted so that an IV bag/s and/or medical equipment can be positioned on either side of the bed 18, without having to lift the carrier assembly 80.

It will be known to those that work in the relevant field that medical equipment, such as monitoring equipment can be of such a weight that lifting is difficult, particularly for those persons that are elderly or are of less than average strength. The carrier assembly 80 allows such persons to change the position of the IV bag/s and medical equipment without danger of injury.

Furthermore, with conventional arrangements, two persons are often required. This is particularly the case where equipment is mounted in both sockets. In such cases, it may be necessary to swap the equipment around. This cannot be done conveniently by one person. The assembly 80 allows equipment simply to be pivoted or swung into a different position.

In a medical or hospital environment it can be difficult to have two persons working at the head of a bed, due to lack of space and interference with equipment. It follows that the assembly 80 can serve to facilitate staff allocation efficiency. This is a significant requirement in places such as hospitals where operational efficiency is desirable.

In the case where one person is working with conventional equipment, that person may be tempted simply to lean over the bed to extract an IV stand from one socket in order to place in the other socket. This can lead to injury. The assembly 80 can obviate that problem.

In this embodiment, the mounting shaft 108 is dimensioned so that the carrier assembly 80 can be mounted in one of the sockets 136, if necessary.

Throughout the specification, including the claims, where the context permits, the term "comprising" and variants thereof such as "comprise" or "comprises" are to be interpreted as including the stated integer or integers without necessarily excluding any other integers.

Use of words that indicate orientation or direction of travel is not to be considered limiting. Thus, words such as "front", "back", "rear", "side", "up", down", "upper", "lower", "top", "bottom", "forwards", "backwards", "towards", "distal", "proximal" and synonyms, antonyms and derivatives thereof have been selected for convenience only. The inventor envisages that various exemplary embodiments of the claimed subject matter can be supplied in any particular orientation and the claimed subject matter is intended to include such orientations.

Various substantially and specifically practical and useful exemplary embodiments of the claimed subject matter, are described herein, textually and/or graphically, including the best mode, if any, known to the inventors for carrying out the claimed subject matter. Variations (e.g., modifications and/or enhancements) of one or more embodiments described herein might become apparent to those of ordinary skill, in the art upon reading this application. The inventors expect skilled artisans to employ such variations as appropriate, and the inventors intend for the claimed subject matter to be practiced other than as specifically described herein. Accordingly, as permitted by law, the claimed subject matter includes and covers all equivalents of the claimed subject matter and all improvements to the claimed subject matter. Moreover, every combination of the above described elements, activities, and all possible variations thereof are encompassed by the claimed subject matter unless otherwise clearly indicated herein, clearly and specifically disclaimed, or otherwise clearly contradicted by context.

The use of any and all examples, or exemplary language (e.g., "such as" and "like") provided herein, is intended merely to better illuminate one or more embodiments and does not pose a limitation on the scope of any claimed subject matter unless otherwise stated. No language in the specification should be construed as indicating any non-claimed subject matter as essential to the practice of the claimed subject matter.

Thus, regardless of the content of any portion (e.g., title, field, background, summary, description, abstract, drawing figure, etc.) of this application, unless clearly specified to the contrary, such as via explicit definition, assertion, or argument, or clearly contradicted by context, with respect to any claim, whether of this application and/or any claim of any application claiming priority hereto, and whether originally presented or otherwise:

a. there is no requirement for the inclusion of any particular described or illustrated characteristic, function, activity, or element, any particular sequence of activities, or any particular interrelationship of elements;

b. no characteristic, function, activity, or element is "essential";

c. any elements can be integrated, segregated, and/or duplicated;

d. any activity can be repeated, any activity can be performed by multiple entities, and/or any activity can be performed in multiple jurisdictions; and e. any activity or element can be specifically excluded, the sequence of activities can vary, and/or the interrelationship of elements can vary.

The use of the terms "a", "an", "said", "the", and/or similar referents in the context of describing various embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Accordingly, every portion (e.g., title, field, background, summary, description, abstract, drawing figure, etc.) of this application, other than the claims themselves, is to be regarded as illustrative in nature, and not as restrictive, and the scope of subject matter protected by any patent that issues based on this application is defined only by the claims of that patent.

The invention claimed is:

1. A medical paraphernalia carrier assembly for carrying medical paraphernalia adjacent a patient care bed, the carrier assembly comprising:
    a mounting arrangement for mounting the carrier assembly on a head of a bed frame intermediate lateral sides of the bed;
    a post that extends from the mounting arrangement,
    a flange being mounted on the post;
    a carrier, a flange being connected to the carrier, the post and the carrier engaging each other so that the post and the carrier can swivel relative to each other with the flanges of the post and the carrier in sliding engagement;
    a holder, a flange being mounted on the holder;
    a support member, a flange being mounted on the support member, the holder and the support member engaging each other so that the holder and the support member can swivel relative to each other with the flanges of the holder and the support member in sliding engagement;
    an extension arm that is connected to the holder and the carrier so that the extension arm can swivel with respect to the post and the support member, the extension arm being of sufficient length to permit functional access from either side of the patient care bed when the extension arm is swung to said either side of the patient care bed;
    a lock pin mechanism for locking the flanges of the post and the carrier in positions relative to each other and for releasing the post and the carrier from each other to swivel; and
    another lock pin mechanism for locking the flanges of the holder and the support member in positions relative to each other and for releasing the holder and the support member from each other to swivel, each lock pin mechanism including a pin that can be pulled to release the flanges from each other and released to lock the flanges to each other.

2. The carrier assembly as claimed in claim 1, in which the mounting arrangement includes a clamp for clamping onto the head of the bed frame.

3. The carrier assembly as claimed in claim 1, in which the flange of the post is mounted intermediate ends of the post, the carrier is tubular, the flange of the carrier is mounted on an end of the carrier and the post is partially received in the carrier to bring the flanges into alignment and sliding engagement with each other.

4. The carrier assembly as claimed in claim 1, in which the pin of each lock pin mechanism projects through one of the flanges and into any one of a plurality of holes along a pitch circle in the other of the flanges that is in sliding engagement with said other of the flanges.

5. The carrier assembly as claimed in claim 4, in which the lock pin mechanisms each include a biasing mechanism that urges the pin into engagement with said other of the flanges, the pin being manually displaceable against a bias of the biasing mechanism to release the flanges to permit swiveling of the flanges relative to each other.

6. The carrier assembly as claimed in claim 1, in which the holder is cylindrical and tubular.

7. The carrier assembly as claimed in claim 6, in which the support member is rotationally mounted on the holder, so that an orientation of the medical paraphernalia can be adjusted when the extension arm is pivoted.

8. The carrier assembly as claimed in claim 7, in which the support member is an elongate support tube.

9. The carrier assembly as claimed in claim 1, in which the flange of the holder is mounted intermediate ends of the holder, the support member is in the form of a support tube, the flange of the support member is mounted on a lower end of the support member and the holder is received through the support tube to bring the flanges into alignment and sliding engagement with each other.

10. A patient care bed that includes a medical paraphernalia carrier assembly as claimed in claim 1.

* * * * *